United States Patent [19]

Badoux

[11] Patent Number: 4,736,757

[45] Date of Patent: Apr. 12, 1988

[54] DENTAL FLOSS HOLDER FOR IMPROVED CLEANING OF INTERDENTAL SPACES

[76] Inventor: Gui Badoux, 232 Chee d'Alsemberg, B-1180 Brussels, Belgium

[21] Appl. No.: 914,351

[22] Filed: Oct. 2, 1986

[30] Foreign Application Priority Data

Oct. 2, 1985 [BE] Belgium ............................... 903358

[51] Int. Cl.$^4$ ............................................. A61C 15/00
[52] U.S. Cl. ..................................................... 132/91
[58] Field of Search ....................... 132/89, 90, 91, 92

[56] References Cited

U.S. PATENT DOCUMENTS

| | | | |
|---|---|---|---|
| 1,306,689 | 6/1919 | Dysart | 132/92 A |
| 2,811,162 | 10/1957 | Brody | 132/89 |
| 4,214,598 | 7/1980 | Lee | 132/92 R |
| 4,427,018 | 1/1984 | Lagace | 435/141 |

Primary Examiner—Robert Peshock
Attorney, Agent, or Firm—Angelo Notaro

[57] ABSTRACT

A dental floss holder with an elongated handle terminating in a pair of furcated opposing prongs with dental floss attached thereto and with an arrangement of slits and grooves at the ends of the prongs for effecting locking of the floss attachment to the ends.

4 Claims, 3 Drawing Sheets

DENTAL FLOSS HOLDER FOR IMPROVED CLEANING OF INTERDENTAL SPACES

BACKGROUND OF THE INVENTION

The invention relates to a device for improving the cleaning of interdental spaces by means of a thread, commonly referred to as dental floss, the device having a single handle and two prongs connected, at one end, to the handle and in which the dental floss extends tightly between the ends opposite the handle.

Dental floss devices have been marketed in the United States under the trademark "FLOSSAID", under the trademark "FLOSSMATE" as marketed by John O. Butler Co. of Chicago, and in a design (see U.S. Pat. No. Des. 216,545) marketed under the trademark "E-Z-FLOSS" by E-Z-Floss of Palm Springs.

The two first-named devices are charged in the same manner: a button-shaped head is fitted to the holder. The leading end of the dental floss has to be wound several times around this head and then installed in a groove along the length of the first prong. The dental floss leaves the prong at its end and joins the end of the other prong. The dental floss has to follow again a groove along this latter prong up to the starting button around which it has to be wound, finally, several times.

The "E-Z-FLOSS" dental floss-holder differs from the two first mentioned designs by the fact that its holder has two heads: one for winding the leading end of the dental floss, the other for winding the trailing end of the floss. Furthermore, the end of this holder features a narrow groove and the floss is secured by combining the windings around the heads with insertions in this groove.

With all three of the aforementioned devices, tensioning of the dental floss is achieved by holding the prongs close together while the dental floss is being installed. These dental floss holders require an expenditure of a considerable length of dental floss for each use, only a small section of which will actually pass between the teeth. Furthermore, since a considerable length of dental floss is under tension, the floss stretches significantly and, therefore, becomes slack. With the two first-named dental floss-holders, the tread sometimes gets out of its groove and gets loose from the ends of the prongs.

Other types of dental floss applicators have been disclosed in U.S. Pat. Nos. 1,623,231, 2,650,598, 3,871,393 and 3,393,687, and British Pat. No. 525,528. Such arrangements do not disclose or subject the structure or advantages achieved by the structure of the present invention.

SUMMARY OF THE INVENTION

The purpose of this invention is to remedy known drawbacks by providing a dental floss holder that consumes only a small amount of dental floss, in which the floss cannot get loose from the ends of the prongs, and which remain tight permanently, by means of a simple method of attachment.

An advantage of this invention is that a dental floss holder allows cleaning of interdental spaces effectively as the dental floss remains tight and solidly secured regardless of the position in which the holder is held. Moreover, the wasteful comsumption of the floss is reduced significantly. Furthermore, the method of loading the dental floss onto the holder is quite simple.

Thus, in accordance with the invention, a dental floss holder is provided for improved cleaning of interdental spaces. The holder includes an elongated handle and a pair of opposed curved prongs. Each prong has a first end flexibly mounted to the handle for movement toward the other. Each prong also has a second free end. Protrusions are formed on inside surface of at least one of the prongs to limit the extent to which the prongs can be moved to each other. Preferably, protrusions are formed on each of the prongs. Upon movement of the prongs toward each other, the protrusions will eventually contact and preclude further movement of the prongs towards each other. A dental floss having a length extended between, and in attachment with, the prongs is provided proximate to the free ends. Gripping means for locking the dental floss in place at the attachment to the prongs is also provided.

The gripping means, in the preferred embodiment of the invention, includes a slit in each prong extending lengthwise from the free end of the prong toward the first end (i.e. attached to the handle) over a length sufficient to form flexible jaws on each side of the slit. Additionally, each prong is provided with a groove that extends about the preiphery of the prong, laterally of the slit, proximate to the free end. A length of dental floss is extended in the slit and a winding of the dental floss, attached to the aforementioned length, is provided in the groove to form the attachment of the dental floss to the free end of each prong.

In accordance with still another preferred feature of the invention, each slit extends at an angle approximately perpendicular to the length of the dental floss extended between the prongs. The jaws are preferably extended towards each other at the free end so that the slit comprises a triangularly tapered cross-section adjacent to free end. Additionally, the surfaces of the jaws adjacent to the slit and the groove are preferably roughened with a series of surface identations and projections in order to improve the adhesion of the dental floss to the jaws.

The slit provided in the prongs has a length sufficient to insure that the slightest pressure applied to the two jaws will close them together over the dental floss. In the preferred arrangement, the groove is located about 3 mm from the end of each prong and the overall structure is dimensioned so that the length of dental floss required to engage the groove and the slit and to extend betwen the prongs is approximately 12 cm. The prongs are pressed together in order to load the dental floss. When released, the prongs tends to resume their normal open position and stretch and tighten the floss around in the grooves at the end of the prongs. This, in turn, firmly closes the slit and locks the floss in place. This locking effect is enhanced by the pressure on the floss during the cleaning of the interdental spaces.

Other advantages of the invention will become apparent to those skilled in the art upon studying of the accompanying specification and drawing.

BRIEF DESCRIPTION OF THE DRAWING

In the accompanying drawing, forming a part of this specification, and in which reference numerals shown in the several views designate like or corresponding parts throughout the same.

DETAILED DESCRIPTION

Figure 1:
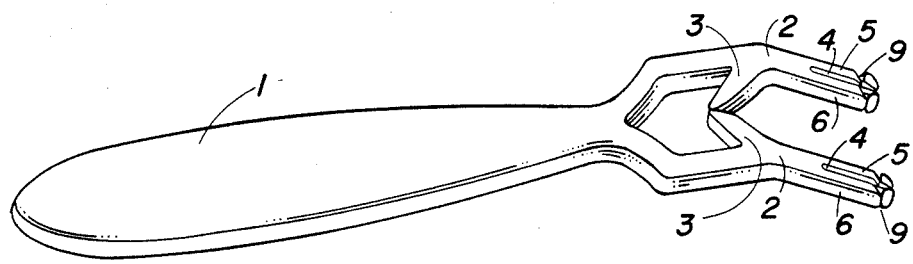
FIG. 1 is a perspective view of a dental floss holder made in accordance with the invention.

As shown in FIG. 1, a dental floss holder made in conformity with this invention comprises a furcated device with an elongated handle 1 and two prongs 2 flexibly mounted to one end of the handle. The arcuate prongs 2 are fitted with protrusions 3. Each of the prongs 2, at its end opposite the handle 1, is slit down its middle lengthwise by a slit 4, to form pincers, over a length sufficient to ensure flexibility so that application of the slightest pressure to the opposed sides 5,6 of the pincer adjacent the slit 4 will cause the sides to press together.

Figure 2:
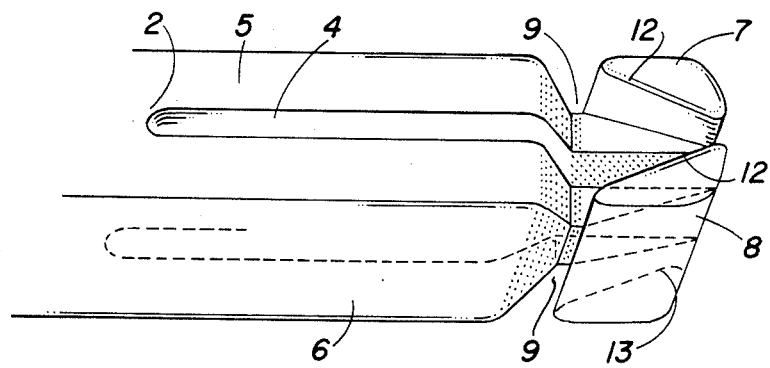
FIG. 2 is an enlarged front perspective view of a portion of the dental floss holder of FIG. 1.
Figure 3:
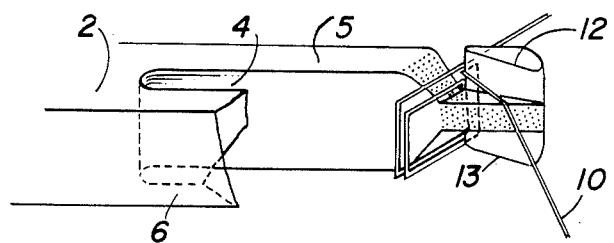
FIG. 3 is a perspective view, partly broken away, of the portion of dental floss holder shown in FIG. 2.

In a preferred embodiment of the invention, each slitted prong preferably is constructed to form a pincer about 12 mm long and the ends 7,8 of the prong, about 3 mm long, will form the jaws of the pincer. Each of the two pincers is provided with a groove 9 which extends laterally relative to the slit 4 around the periphery of each prong about 3 mm from the end opposite the handle FIGS. 2 and 3 illustrate an enlarged view of part of the end of one prong. FIG. 3 also illustrates the manner in which the floss is arranged at the end of a prong.

In operation, a user will need about 10 to 12 cm of dental floss to load the device. This length can be measured by means of markings on the handle of the holder or by color marks on the dental floss itself.

Figure 4:
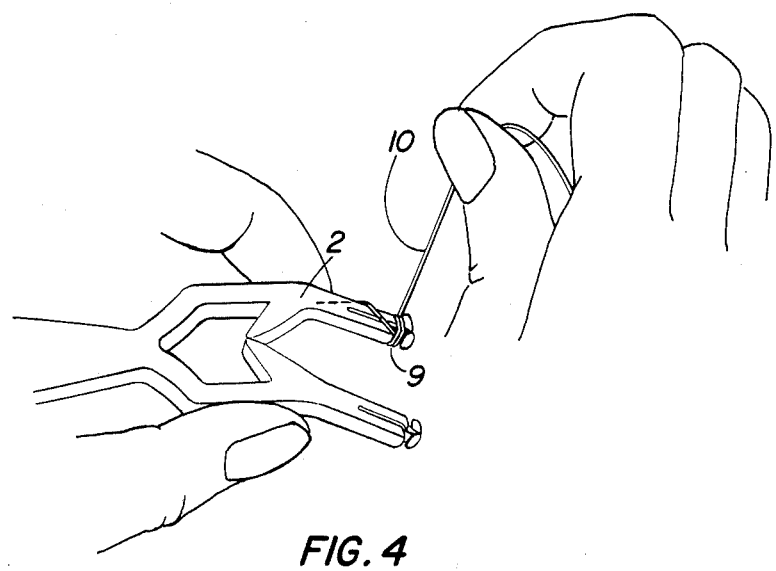
FIGS. 4 though 7 pictorially illustrate a sequence of the steps utilized in loading a floss onto the dental floss holder of FIG. 1.
Figure 5:
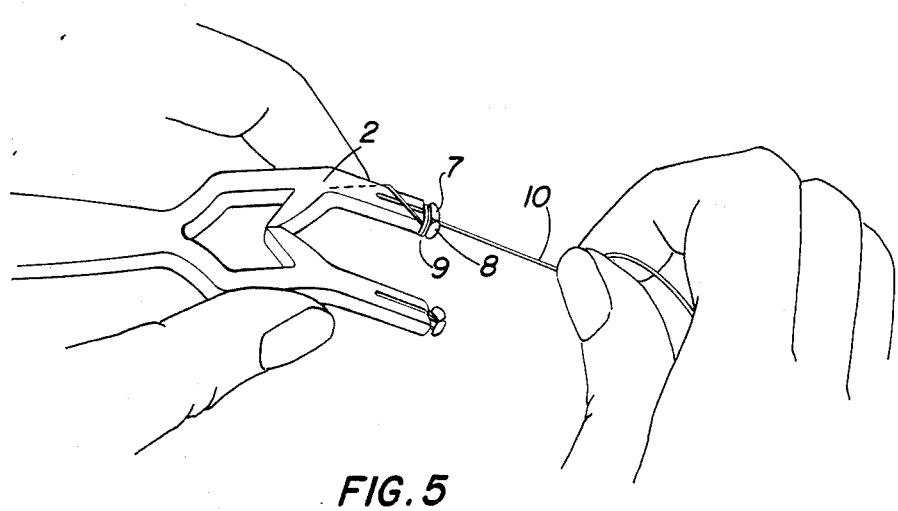
Figure 6:
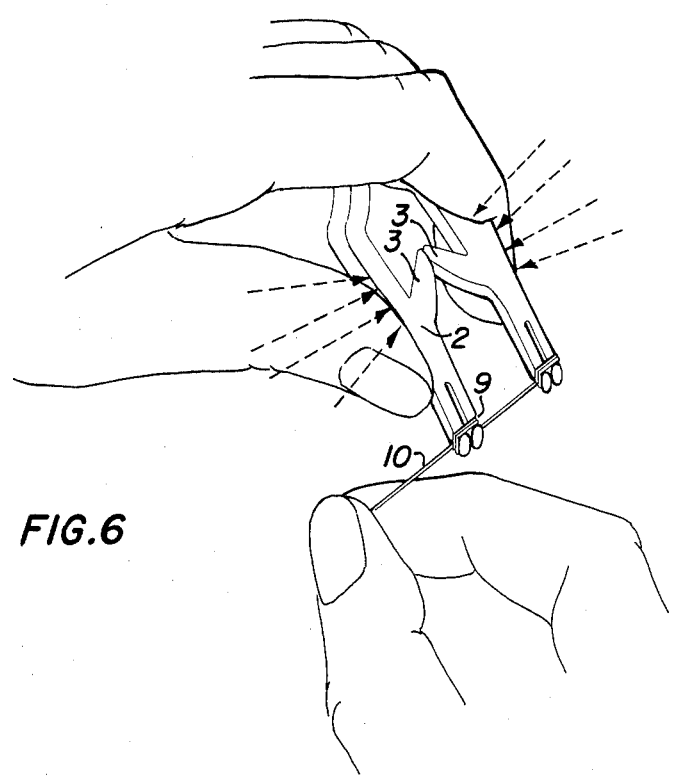
Figure 7:
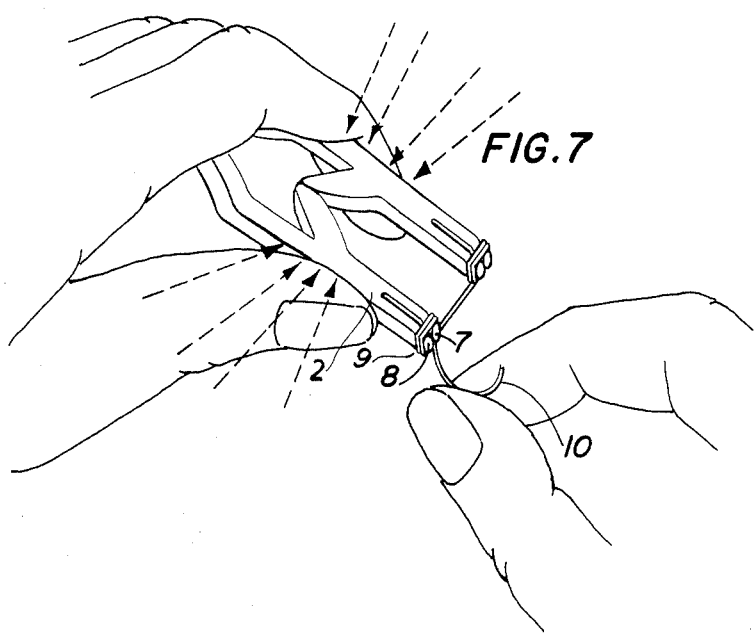

As shown in FIG. 4, the user winds the leading end of the floss 10 around the groove 9 at the end of prong 2 about three times. The user then inserts floss into the slit between the jaws (see FIG. 5). As shown in FIG. 6, while keeping the prongs tightly together until protrusions 3 abut, the user winds the floss thrice around in groove 9 at the end of the second prong. Before releasing the prongs, as best shown in FIG. 7, the user passes the end of the floss into the slit between jaws 7,8 of the second prong.

Each set of semi-prongs 5,6 is self-locking. When the user releases the prongs, after having loaded the device as described above, the prongs tend to resume their normal open position and thus stretch the floss, which tightens the windings in the grooves 9 and thus locks the jaws 7,8 of each prong onto the floss. Any pull on the floss while cleaning the interdental spaces will increase the grip even more. The slit in each prong is approximately perpendicular to the tightened floss. Thus, the slipping of the floss is prevented by the increased gripping effect, which arises by virtue of its being held in a plane approximately perpendicular to the pull. The movement of the jaws 7,8, in a direction parallel to the pull of the floss, enhances the gripping effect, particularly while the device is in use. Finally, the floss is also locked into position by the groove itself, which is at a right angle to the slit. For the purpose of inserting the thread into the jaws 7,8 the user will have to pull the thread in a direction perpendicular to the plane of the winding in the groove 9.

The sides 12,13 of the jaws 7, 8 are triangularly tapered, relative to the slit, in a manner that allows the floss to slide easily between the jaws 7,8 after having been wound in the groove 9.

The adherence of the floss can be increased by roughening the surface areas of the jaws 7,8 adjacent the slit 6 and groove 9.. The surface areas, for example, are covered with small projections or dots as shwon in FIGS. 2 and 3.

The invention claimed is:

1. A dental floss holder for improved cleaning of interdental spaces, comprising an elongated handle and a pair of opposed curved prongs, each prong having a first end flexibly mounted to the handle for movement toward each other and having a second free end, protrusion means mounted to at least one of the prongs to limit the extent to which the prongs can be moved toward each other, a dental floss having a first length extended between and in attachment with the prongs proximate the free ends, gripping means for locking the dental floss in place at the attachment to the prongs, and wherein the gripping means comprises a slit in each prong extending lengthwise from the free end of the prong toward the first end over a length sufficient to form a pincer portion having flexible jaws on opposite sides of the slit, each prong including a groove extended about the periphery of the prong, laterally of slit, proximate to the free end, and further comprising a second length of the dental floss extended in the slit and a winding of the dental floss in the groove connected to the second length comprises the attachment.

2. A dental floss holder, according to claim 1, wherein each slit extends at an angle approximately perpendicular to the first length of the dental floss extended between the prongs.

3. A dental floss holder, according to claim 1, wherein the jaws are extended toward each other at the free end so that the slit comprises a triangularly tapered cross-section adjacent the free end.

4. A dental floss holder, according to claim 1, wherein the prongs comprise the surface areas adjacent the slit and the groove, said surface areas including a rough surface whereby the adhesion of the floss to the surface areas is improved.

* * * * *